(12) United States Patent
Dring et al.

(10) Patent No.: US 8,154,413 B2
(45) Date of Patent: Apr. 10, 2012

(54) SYSTEM AND METHODS FOR MONITORING CAREGIVER PERFORMANCE

(75) Inventors: Barton Dring, River Forest, IL (US); John Ross, Elmhurst, IL (US)

(73) Assignee: ProactiCare LLC, Hinsdale, IL (US)

( * ) Notice: Subject to any disclaimer, the term of this patent is extended or adjusted under 35 U.S.C. 154(b) by 28 days.

(21) Appl. No.: 12/455,347

(22) Filed: Jun. 1, 2009

(65) Prior Publication Data
US 2010/0057543 A1   Mar. 4, 2010

(51) Int. Cl.
*G08B 23/00* (2006.01)

(52) U.S. Cl. ............... 340/573.1; 340/533; 340/539.16; 340/665; 600/595

(58) Field of Classification Search ............... 340/573.1, 340/573.4, 561, 562, 539.1; 600/587, 595
See application file for complete search history.

(56) References Cited

U.S. PATENT DOCUMENTS

| | | | |
|---|---|---|---|
| 3,439,358 A | 4/1969 | Salmons | |
| 4,228,426 A | 10/1980 | Roberts | |
| 4,295,133 A | 10/1981 | Vance | |
| 4,320,766 A | 3/1982 | Alihanka et al. | |
| 4,565,910 A * | 1/1986 | Musick et al. | 200/85 R |
| 4,633,237 A | 12/1986 | Tucknott et al. | |
| 4,638,307 A | 1/1987 | Swartout | |
| 4,700,180 A | 10/1987 | Vance | |
| 4,796,013 A * | 1/1989 | Yasuda et al. | 340/562 |
| 4,827,763 A | 5/1989 | Bourland et al. | |
| 4,907,845 A | 3/1990 | Wood | |
| 5,235,319 A | 8/1993 | Hill et al. | |
| 5,353,012 A | 10/1994 | Barham et al. | |
| 5,410,297 A | 4/1995 | Joseph et al. | |
| 5,471,198 A | 11/1995 | Newham | |
| 5,519,380 A | 5/1996 | Edwards | |
| 5,633,627 A | 5/1997 | Newham | |
| 5,699,038 A | 12/1997 | Ulrich et al. | |
| 5,780,798 A | 7/1998 | Hall-Jackson | |
| 5,808,552 A * | 9/1998 | Wiley et al. | 340/573.4 |
| 6,025,782 A | 2/2000 | Newham | |
| 6,078,261 A | 6/2000 | Davsko | |
| 6,111,509 A | 8/2000 | Holmes | |
| 6,133,837 A | 10/2000 | Riley | |
| 6,208,250 B1 | 3/2001 | Dixon et al. | |
| 6,252,512 B1 | 6/2001 | Riley | |
| 6,297,738 B1 | 10/2001 | Newham | |
| 6,307,476 B1 | 10/2001 | Smith et al. | |
| 6,329,913 B1 * | 12/2001 | Shieh et al. | 340/562 |
| 6,362,725 B1 | 3/2002 | Ulrich et al. | |
| 6,384,728 B1 * | 5/2002 | Kanor et al. | 340/573.1 |
| 6,546,813 B2 | 4/2003 | Hubbard, Jr. | |
| 6,778,090 B2 | 8/2004 | Newham | |
| 6,784,797 B2 | 8/2004 | Smith et al. | |
| 6,788,206 B1 | 9/2004 | Edwards | |
| 2002/0151990 A1 | 10/2002 | Ulrich et al. | |
| 2003/0136201 A1 | 7/2003 | Hubbard, Jr. | |
| 2003/0187618 A1 | 10/2003 | Inda et al. | |
| 2003/0227386 A1 | 12/2003 | Pulkkinen et al. | |

(Continued)

*Primary Examiner* — Thomas Mullen
(74) *Attorney, Agent, or Firm* — Valauskas Corder LLC

(57) ABSTRACT

Systems and methods for monitoring the performance of a caregiver are disclosed. The systems may be configured to monitor the movement of each subject in a network of subjects. One such system includes a plurality of strips adhered in spaced-apart relation on a mattress pad, upon which a subject is positioned. One or more transmitter is provided coupled to the plurality of strips. A processor is connected to the one or more transmitter. The processor is provided with operating software to record and report caregiver activity or both caregiver activity and subject activity.

13 Claims, 20 Drawing Sheets

U.S. PATENT DOCUMENTS

2004/0046668 A1 3/2004 Smith et al.
2004/0111045 A1* 6/2004 Sullivan et al. ............... 600/595
2005/0011738 A1 1/2005 Smith et al.
2006/0028350 A1 2/2006 Bhai

* cited by examiner

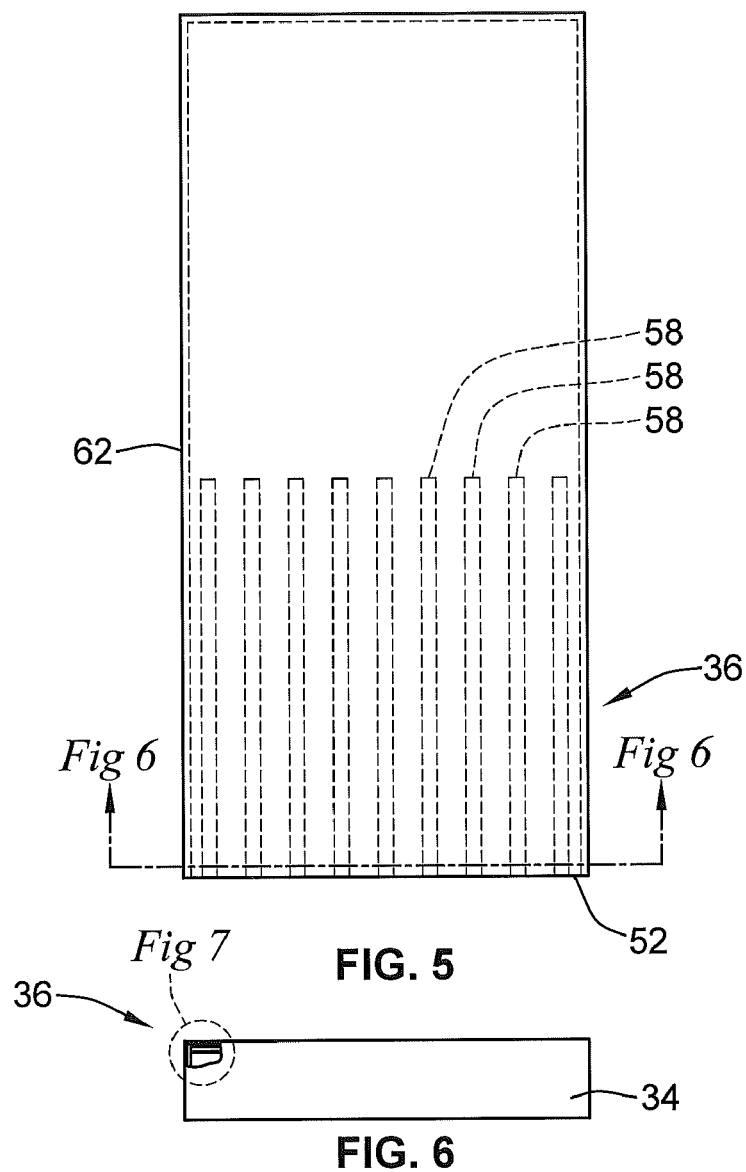
FIG. 5
FIG. 6
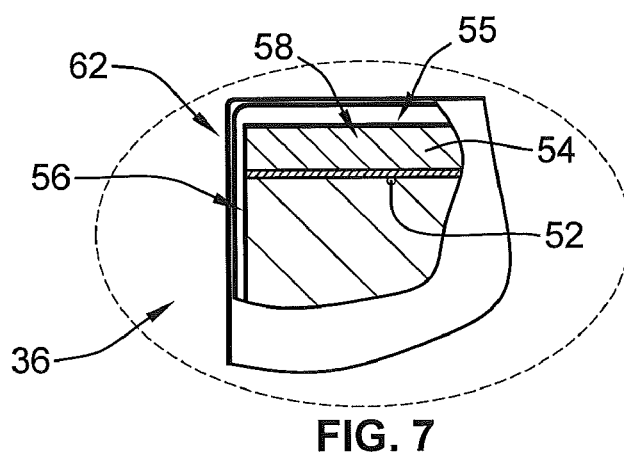
FIG. 7

DCT Software Flowchart

DCT Server Flowchart

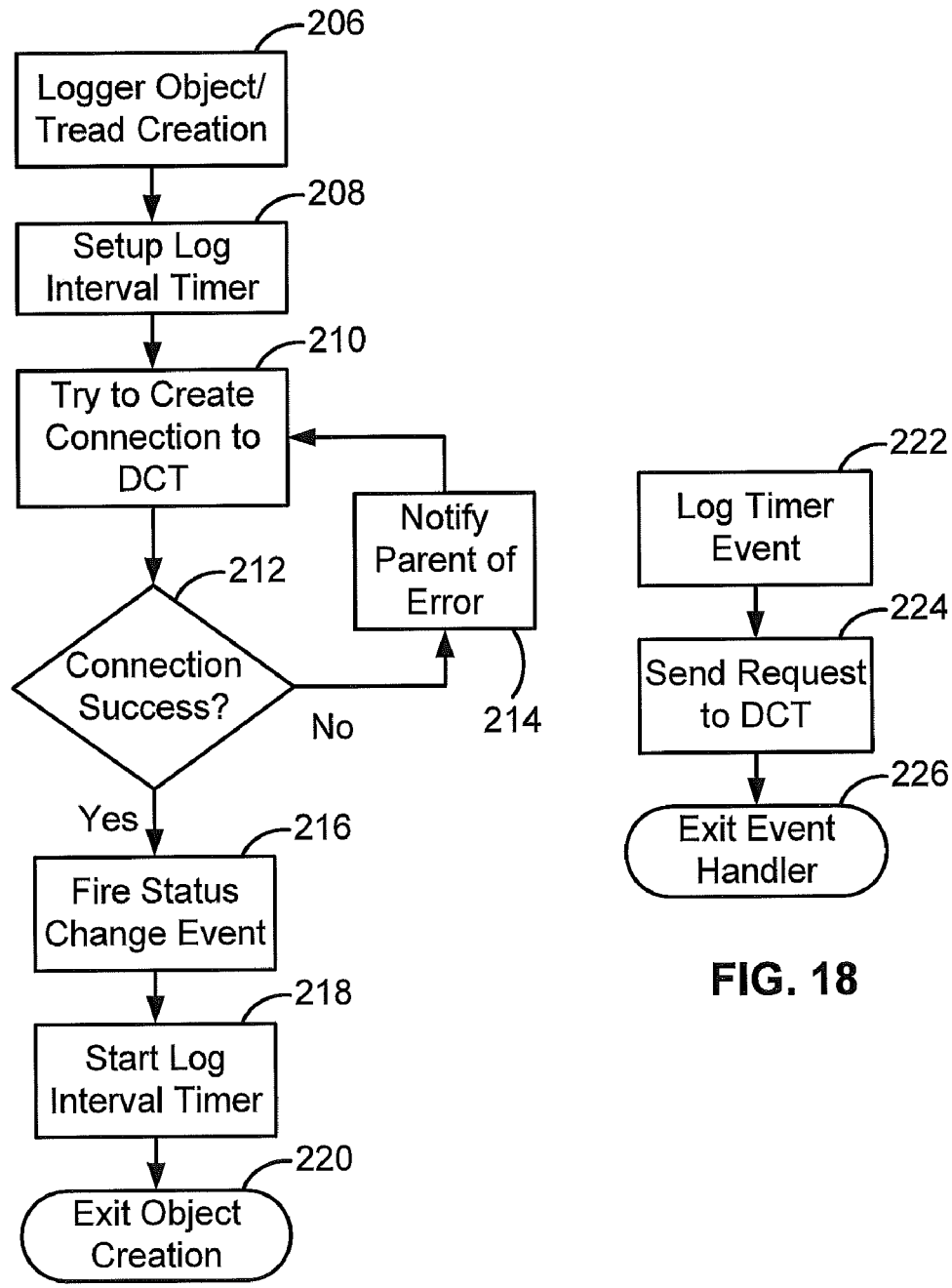

1120 Room Group Activity Report

ProactiCare
*Where technology meets compassion*™

Patient Care Quality Management System

FACILITY: ABC Health Care   LOCATION: Hinsdale, IL

Home

24 Hour Facility Activity Report
Period Ending: 8:00AM, Saturday, April 1, 2006

◁ PREVIOUS    (CALENDAR) (TODAY)    NEXT ▷

Patient Count: 4

North - Patients In Analysis: 4

| WARNING | 1 | | 15% |
| CAUTION | 5 | | 48% |
| ACCEPTABLE | | | 37% |

South - Patients In Analysis: 0

West - Patients In Analysis: 0 user: admin    Logout | Help | Reports | Administration

1310 Patient Status Report

| | Patient Name | Room Group | Room | Bed |
|---|---|---|---|---|
| 🖉 📄 📇 | Jacobs, Jenny | North | 10 | 123 |
| 🖉 📄 📇 | Jones, Jim | North | 10 | 12 |
| 🖉 📄 📇 | K., Gloria | South | 30 | 1 |
| 🖉 📄 📇 | L., Grace | North | 5 | 1 |
| 🖉 📄 📇 | M., John | North | 10 | 1 |
| 🖉 📄 📇 | N., Wilma | North | 4 | 1 |
| 🖉 📄 📇 | Norvid, Peter | West | 1 | 133 |
| 🖉 📄 📇 | O., Peter | North | 22 | 1 |
| 🖉 📄 📇 | Ranch, Roy | North | 10 | 3 |
| 🖉 📄 📇 | S., Demetria | North | 5 | 1 |
| 🖉 📄 📇 | Sim, John | North | 10 | 1 |
| 🖉 📄 📇 | Wade, P | North | 10 | 1 |
| 🖉 📄 📇 | X_Moore, Betsy | West | 3 | 1 |
| 🖉 📄 📇 | X_Simpson, Victoria | West | 2 | 1 |
| 🖉 📄 📇 | X_Smith, Donna | West | 1 | 1 |

1320 Monitor Status Form

ProactiCare
Where technology meets compassion™

Patient Care Quality Management System

FACILITY: ABC Health Care  LOCATION: Hinsdale, IL

Home > Reports > Patient Monitoring Reports

| Patient Name | Room Group | Room | Bed | Caution Time (mins) | Warning Time Bed | Empty Level | Turn/Out Paging | Monitoring |
|---|---|---|---|---|---|---|---|---|
| Jacobs, Jenny | North | 10 | 123 | 120 | 150 | 4500 | ○ ○ 18:00 - 08:00 | ● |
| Jones, Jim | North | 10 | 12 | 120 | 150 | 4500 | ○ ● 00:00 - 24:00 | ● |
| K., Gloria | South | 30 | 1 | 120 | 150 | 4700 | ● ● | ○ |
| L., Grace | North | 5 | 1 | 120 | 150 | 4200 | ● ● | ○ |
| M., John | North | 10 | 1 | 120 | 150 | 4000 | ● ● | ● |
| N., Wilma | North | 4 | 1 | 120 | 150 | 5000 | ● ● | ● |
| Norvid, Peter | West | 1 | 133 | 2 | 10 | 4300 | ○ ○ 00:00 - 24:00 | ○ |
| O., Peter | North | 22 | 1 | 120 | 150 | 4500 | ● ● | ● |
| Ranch, Roy | North | 10 | 3 | 120 | 150 | 4500 | ○ ○ 18:00 - 08:00 | ● |
| S., Demetria | North | 5 | 1 | 120 | 150 | 4700 | ● ● | ● |
| Sim, John | North | 10 | 1 | 120 | 150 | 4500 | ○ ○ 00:00 - 24:00 | ● |
| Wade, P | North | 10 | 1 | 2 | 4 | 5500 | ○ ○ 00:00 - 24:00 | ○ |
| X_Moore, Betsy | West | 3 | 1 | 120 | 150 | 4500 | ● ● | ● |
| X_Simpson, Victoria | West | 2 | 1 | 120 | 150 | 4500 | ● ● | ● |
| X_Smith, Donna | West | 1 | 1 | 120 | 150 | 4500 | ● ● | ● | user: admin    Logout | Help | Reports | Administration

1410 Patient Administration Entry Form

ProactiCare
Where technology meets compassion™

Patient Care Quality Management System

FACILITY: ABC Health Care   LOCATION: Hinsdale, IL

Home > Administration > Patient Administation

New Paient Entry Form

| | | |
|---|---|---|
| Last Name | [        ] | 50 chars max. |
| Frist Name | [        ] | 50 chars max. |
| Room Group | North ▼ | Select this before room |
| Room | 10 ▼ | |
| bed | [  ] | |
| Caution Level | 120 | minutes |
| Warning Level | 150 | minutes |
| Empty Level | 4500 | |
| Turn Paging | ☐ | |
| Out of Bed Paging | ☐ | |
| Page time window | 18:00 to 08:00  24hr | (xx:xx Use 24hr format) |
| Turn Page Comment | [        ] | Appended to turn pages |

[ Enter New Patient ]

- Edit Existing Patient -

Select Name to Edit  | Jacobs, Jenny ▼ [Edit] [Delete] ☐ Comfirm Delete

1510 New Bed Monitor Entry Form

| ProactiCare<br>Where technology meets compassion™ | Patient Care Quality Management System |

FACILITY: ABC Health Care   LOCATION: Hinsdale, IL
Home > Administration > Patient Administation New Paient Entry Form

| Serial Number | [          ] | See bottom of monitor |
| Address | 192.168.[   ].[   ] | Network Address of Montior |
| Port | [Wireless ▼] | Select Network Port |
| Query Rate | [500 ▼] | milliseconds |
| Max. Log Interval | [20 ▼] | seconds |
| Patient | [-Not Assigned ▼] | |
| Active | ☐ | Monitor Will Log Data (active) |

[ Enter New Monitor ]

- Select Existing Monitor to Edit -

Select Monitor S/N  [12 (M., John) ▼] [Edit] [Delete] ☐ Comfirm Delete user: admin            Logout | Help | Reports | Administration

1610 Edit Room Groups Form

ProactiCare
Where technology meets compassion™

Patient Care Quality
Management System

FACILITY: ABC Health Care   LOCATION: Hinsdale, IL

Home > Administration > Facility Setup > Edit Room Groups

Select a Task

| Add Room Group | Edit/Delete Existing Room Group(s) | user: admin          Logout | Help | Reports | Administration

SYSTEM AND METHODS FOR MONITORING CAREGIVER PERFORMANCE

PRIORITY STATEMENT

This continuing patent application claims the benefit of Non-Provisional U.S. patent application Ser. No. 11/133,405 filed May 19, 2005, now U.S. Pat. No. 7,541,935.

FIELD OF THE INVENTION

The present invention relates to systems and methods for monitoring subjects, such as human subjects. More particularly, the present invention relates to systems and methods for monitoring and reporting caregiver performance in a healthcare setting related to care of a subject on a subject support device, such as on a hospital bed or nursing home bed.

BACKGROUND OF THE INVENTION

Many subjects in nursing homes may not have the physical capability to turn or reposition themselves in a bed and in such a case, depend upon staff members, typically a Certified Nursing Assistant (CNA) or other caregiver, to move them. This scenario may also occur in a hospital or similar setting. In many instances, it is a requirement or medical necessity that the subject be turned in bed frequently, at a specified interval, such as for example, every two hours, to prevent the development of tissue or skin breakdown, which can severely compromise health, comfort, and quality of life. Failure to periodically move the subject can result in what is commonly known as pressure sores or "bedsores".

What is needed is a system and method that can monitor the movement of a subject, patient or resident, (hereinafter referred to simply as "subject") so that movement of the subject can be detected, tracked, recorded and reported. Accordingly, systems have become available which alert a caregiver when a subject has moved or left the bed. Some of these systems have sophisticated means of determining the position of the subject on the bed. As used herein, the terms "CNA" and "caregiver" are used interchangeably and refer to a person providing care to an individual subject or subjects. Such a system and method may be used to monitor when a subject leaves and returns to the bed and detect and monitor patterns of movement. In many cases, subjects are unable to stand or walk from their bed unaided; however, these subjects attempt to exit their bed in a weakened condition and are at risk of falling and associated injuries. The system has the inherent ability to provide a signal when a subject has exited their bed and will notify the responsible caregiver of this situation.

These systems do not have a means to allow nursing home administrators, hospital supervisors or healthcare managers (hereinafter referred to as "clients") to confirm that a CNA or the like has performed his or her duty to move the monitored subject. The present invention addresses this need.

SUMMARY OF THE INVENTION

The present invention is directed to systems and methods for monitoring the performance of a caregiver. Simultaneously, the present invention is directed to systems and methods for monitoring the movement of each subject in a network of subjects and the response of the caregiver.

One system is shown to include a plurality of sensors, preferably in the form of strips disposed in spaced-apart relation to a mattress pad. The strips extend longitudinally from the head end of the mattress pad. The mattress pad is configured to be placed on top of a mattress, and to then be covered by a standard nylon slip-cover or the like that fits over the mattress and the mattress pad.

All software aspects of the invention have been written to be portable to multiple operating systems and hardware platforms. Open source applications and development tools have been used to limit downstream system, licensing and development costs. Web browser based data entry and reporting systems have been used to reduce client costs and allow users to interact with the system on familiar interfaces and hardware. It also allows handheld devices, pagers, cell phones, tablet PCs, etc. to be used without additional software development costs. Raw data is always stored so future enhanced data analysis tools have access to the original data. Multiple levels of security are used to protect the integrity and confidentiality of the data.

This system may include hardware and functionality in order to function as a bedside based undergarment moisture detector. In such a case, transmission of moisture data from patient undergarment to bedside would be performed via Wireless link such as RFID, ZigBee™, IR, Bluetooth™, etc. A small probe, such as a very thin wire is penetrated through the outer plastic surface into absorbency material. The probe could be designed to penetrate the backside of undergarment and be positioned where it could detect moisture. A very thin wire could run from the sensor to a small transmitter which would be attached to the front undergarment waistline of the subject. This front side transmitter could be a low cost, high efficiency, reusable transmitter which would enable data to be transmitted area wide or to the bedside DCT. At a predetermined value, the CNA could be notified that the subject was in need of an undergarment change. The major advantage that the CNA would no longer need to perform periodic checks, but only when specifically needed.

A nurse call module is provided and is adapted to be used as a device able to detect when a nurse call is placed on a conventional system and when it is answered. As the call is placed, the inline module detects a nurse call signal and then independently sends this signal back to the bedside DCT which then transmits it to the central processor where it is time and date stamped, and then incorporated into the database relative to the patient and/or DCT ID. In addition to the conventional audio and visual signals generated during a nurse call, the system also pages, emails or notifies via mobile phone that a subject is in need of assistance. Once the care has been rendered, the CNA would switch off the bedside nurse call device which would also signal the central processor to stamp the database with a time and date. The proposed device would be an in-line component which would be "jacked" into the wall and then the nurse call connector would be snapped into this device. The central processor could communicate to the DCT or other type of bedside transmitter via a hard wire or wireless connection. The major advantage of the system of the present invention is that the existing nurse call system would perform as intended, with the added advantage of verifiable care giver performance response time, thus allowing a better method of caregiver quality control.

A proposed system could also act as a bed alarm, monitoring when the bed is occupied or when it is empty, thus allowing the caregiver to be notified when a high risk "fall" subject is out of bed and in danger of falling while unattended. This warning system could be linked to the existing in-house audio and visual indicators as well as nurse station computer screen notification in addition to mobile phone, pager and other communication systems.

The DCT has an excess of bandwidth in both its wireless and hardwired configurations. This additional capacity combined with its current function as a bedside data collection and transmission device provides tremendous opportunities for additional in-room capabilities. Some of these concepts include voice, data and video communication, including a room call and patient audio and video monitoring. Other capabilities include high bandwidth devices such as sensors or monitors plus in-room internet connectivity.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

A detailed description particularly refers to the accompanying figures in which:

FIG. 5 is a top plan view of a mattress pad and sensors covered by a mattress cover according to another embodiment of the present invention;

FIG. 6 is an elevation view of the mattress pad of FIG. 5 and a mattress, both of which are covered by a mattress cover;

FIG. 7 is a cutaway view of part of FIG. 5, showing the mattress, mattress pad, and fastener, all of which are covered by the mattress cover;

FIGS. 13-20 each show a subset of operational steps of the data server software according to a method of operation of the present invention;

FIG. 23 shows a "View Room Groups Page" according to an embodiment of the present invention;

FIG. 24 shows a "Patient Reports Page" according to an embodiment of the present invention;

FIG. 25 shows a "Monitor Reports Page" according to an embodiment of the present invention;

FIG. 27 shows a "Patient Administration Entry Form Page" according to an embodiment of the present invention;

FIG. 28 shows a "New Bed Monitor Entry Form Page" according to an embodiment of the present invention;

FIG. 29 shows an "Edit Room Groups Form Page" according to an embodiment of the present invention.

DETAILED DESCRIPTION OF EMBODIMENTS OF THE INVENTION

Figure 1:
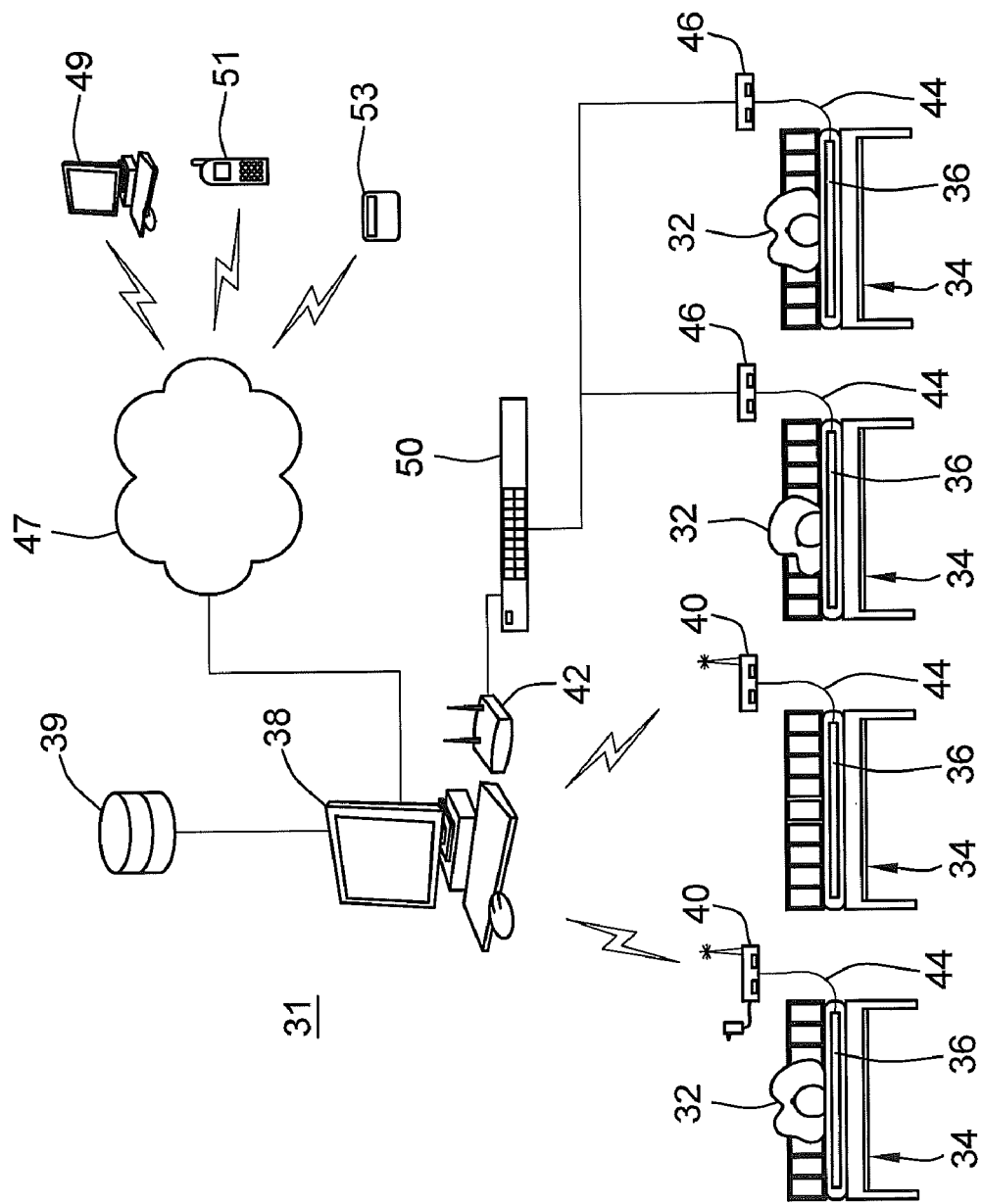
FIG. 1 is a schematic view of the monitoring system.

A system 31 for monitoring the performance of a caregiver relative to movement of a single subject 32 or a plurality of subjects 32 is shown in FIG. 1. Illustratively, subject 32 is positioned on a bed 34, but it should be understood that other subject support devices, such as chairs, wheelchairs, or the like, are within the scope of the invention. Accordingly, all of the attributes of the system 31 described herein can be applied to any type of subject support device.

As shown in FIG. 1, system 31 includes a plurality of beds 34, each having a sensor 36 that is in communication with a central processor 38, such as that which can be found in the computer shown in FIG. 1. The sensor 36 may be a single sensor or preferably a sensor array including a plurality of individual or separate sensor units. The central processor 38 may take the form of other computing devices having the capability of detecting changes in the status of sensors 36 and outputting an alarm, notice or report, for example. The system 31 preferably uses a web browser based reporting system. Reports are generated on a web server (not shown) and viewed on standard web browsers with no special software required. The data is presented in a hierarchical fashion giving a quick overview as well as the ability to drill down to the lowest level of interest. The reporting system is designed to quickly identify areas of the facility that may need attention. Other functions—such as a data gathering device—of the central processor 38 will be explained in more detail below.

The sensors 36 may include electrically conductive strips, which when they are brought into proximity or are permitted to disconnect, undergo a change of state with respect to, for example, opening or closing a circuit.

Other sensors are also contemplated that are capable of sensing a change of position or status of a subject, such as pressure sensors, heat sensors, and so on. The sensors 36 may include conductive material, such as conductive paint, plastic, metal or any other material that when triggered functions to register or detect a change of status of a subject operatively associated with the sensor and generate or permit the generation of a signal or event therefor.

Sensors 36 may communicate with central processor 38 via a wireless (WiFi) connection. Transmitter 40 is shown as a wireless transmitter whereas transmitter 46 is shown as a wired transmitter that both communicate with a base station 42 that is connected with central processor 38. The transmitters, both shown at 40 and 46, and based on a Motorola IC, part no. 33794, are also referred to herein as a data collector transmitter (DCT) unit, which is a slave device that transmits data to a master device (referred to herein as the central processor 38) using a predefined protocol. The protocol is designed to be compatible with a wide range of networks including, but not limited to RS232, multi-drop RS485 as well as higher level networks such as Ethernet, Bluetooth™, ZigBee™, 802.15.4 and WiFi. Addressing and error detection is provided at the lowest level of the protocol for use on simple RS485 type networks.

The central processor 38 collects data from the slave DCT units 40, 46. The central processor 38 requests data from each DCT unit 40, 46 at the desired data rate. Preferably, the data processor 38 is a networked PC running applications designed to communicate with as many as several hundred DCT units 40, 46 at the same time. It is a multi-threaded, object oriented, fault tolerant program that can recover from network and DCT units 40, 46 problems in real time without affecting data gathering on the rest of the system 31. The central processor 38 may store all data into a standard SQL relational database 39.

The central processor 38 may be a standard PC running a Java application. The program reads and writes to a database 39. The central processor 38 uses conventional programming to interface with the database 39, so portability to other databases is possible. The central processor 38 polls the database 39 at regular intervals to determine the number of clients (DCT units or installations) it needs to communicate with. Each DCT unit 40, 46 has a unique address and communication rate stored in the database 39. The device and the applications running thereon are multi-threaded so problems with individual devices and network latency do not affect other devices and program performance. If one transmitter 40, 46 is not responding, all other devices will still return data at the predetermined rate. The central processor 38 will continue to try to regain communication with the non-responsive slave until it is successful or the entry in the database is removed. The data received from the transmitters 40, 46 is stored in the database 39. The data is time stamped and referenced to the transmitters 40, 46. To reduce the database growth, if there is no movement by the subject, or if the subject is no longer in bed, the recorded sensor values will be at wider intervals. However, once movement is again detected, the system will be triggered to begin collecting data at a more rapid and predetermined pace allowing full resolution of the subject movement. Even if the minimum change amount has not occurred, data will at least be stored at a predetermined interval such as once every 10 seconds, for example, or at any suitable interval. The central processor 38 is intended to run autonomously.

The sensor 36 is connected to the DCT 46, which includes a microcontroller. The microcontroller has custom software written in the C programming language. The microcontroller constantly polls the sensor 36 looping between the 9 electrodes of the sensor 36 using one of several built in 10-bit analog to digital channels. The microcontroller can calibrate the system to adjust the output of the electrodes so they all read roughly the same value when no subject 32 is in the bed 34. It can also adjust the high and low end points of the sensor values to use the full 10-bit range. The calibration values are stored in non-volatile EEPROM so they are not lost if the power is interrupted or removed. The read values are adjusted by the stored calibration and stored in RAM. The values in RAM are then used to quickly respond to the master device when requested.

All communication is done with the microcontroller using a serial data protocol. The protocol uses an 8-bit address and a 16-bit CRC to insure data integrity. While the address and CRC are not needed with higher-level networks like Ethernet, they allow the use of future, simpler networks like RS485. The DCT units 40, 46 currently uses an OEM serial to Ethernet device (not shown), but another embodiment includes integration into the microcontroller.

Although wireless transmitters 40 are shown in FIG. 1 to be separate from sensors 36, and connected with a harness 44, it is within the scope of the invention to combine the wireless transmitter 40 with the sensor or to place it in other locations, such as within a bed mattress. Wireless transmitters 40 are illustratively capable of collecting data from their associated sensors 36. The system 31 is preferably configured so as to be capable of handling upwards of a hundred beds or more that may comprise a hospital network or a nursing home network, for example.

As an alternative, a transmitter 46 may be used, the transmitter 46 having a wired (e.g., Ethernet) connection with central processor 38. Illustratively, transmitter 46 uses an Ethernet network consisting of Ethernet cables and an Ethernet hub 50 that is in communication with central processor 38. Of course, system 31 may include both wireless and Ethernet elements, and may be connected via other means and/or protocols, such as coaxial cable, electrical wires, radio frequency, Bluetooth™, ZigBee™, 802.15.4 or any other manner for communicating data that is known in the art.

As can be seen in FIGS. 2-7, sensor 36 comprises a mattress pad 54 having an array of parallel conductive fabric strips 58 adhered thereto. Strips 58 extend longitudinally along the mattress pad 54, starting at the head end 60. A fastener 52 may be coupled to one end of each of the strips 58 at the head end 60 of the mattress pad 54. While the illustrated embodiment contemplates the adhesion of the strips 58 to an upper surface or top side 64 of the mattress pad 54, it should be understood that other configurations and fastening methods are within the scope of the invention, including the placement of the strips 58 within the pad 54, or on top of another surface such as directly on top of a mattress 56.

In the illustrated embodiment, strips 58 are evenly spaced at an interval A (shown in FIG. 3), such as four inches. Strips 58 are illustratively width B, which is approximately one inch in the presently shown embodiment.

Mattress pad 54 is illustratively a half-inch thick urethane foam pad that is cut to the same dimensions as a mattress 56 on which it is to be positioned. Such urethane foam is flame retardant, thereby meeting the FF 4-72 (cigarette test) standards for flammability set forth by the Consumer Product Safety Commission. Furthermore, the foam preferably conforms to the California Technical Information Bulletin No. 117 regarding combustibility.

In the illustrated embodiment, nine strips 58 are positioned in parallel orientation to run longitudinally from the head end 60 of mattress pad 54. Each of the strips has an adhesive bottom surface (not shown) that is configured to adhere to the mattress pad 54. The adhesive surface is illustratively a pressure sensitive adhesive (PSA), however, other adhesives are within the scope of this invention. After each of the strips 58 is adhered to a top side 64 of the mattress pad 54, the entire mattress pad is overlaid with a flame retardant polyester cloth 55, (FIG. 7) thereby capturing the strips 58 and functioning so that the strips remain securely in place throughout the life of the mattress pad 54.

Strips 58 may be any suitable thickness, such as approximately 0.008 inches thick and made of a conductive laminated fabric. The laminated fabric is flame retardant with a UL 94 V-0 rating. One example of such a fabric is manufactured by Laird Technologies of St. Louis, Mo.

As can best be seen in FIGS. 5-7, which shows another embodiment of a portion of the present invention, an outer mattress cover 62 is positioned over mattress 56 and overlying mattress pad 54 so that the entire sensor 36 is removed from direct contact with sheets or a subject. Mattress cover 62 is preferably a standard nylon covering used over a standard nursing home mattress.

Figure 2:
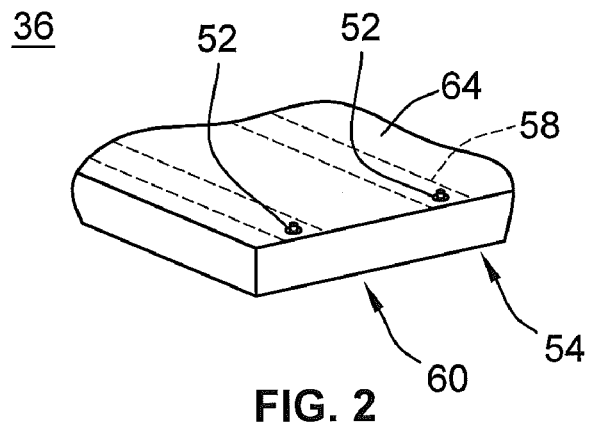
FIG. 2 is a cutaway perspective view of the head end of a mattress pad with sensors according to an embodiment of the invention.
Figure 3:
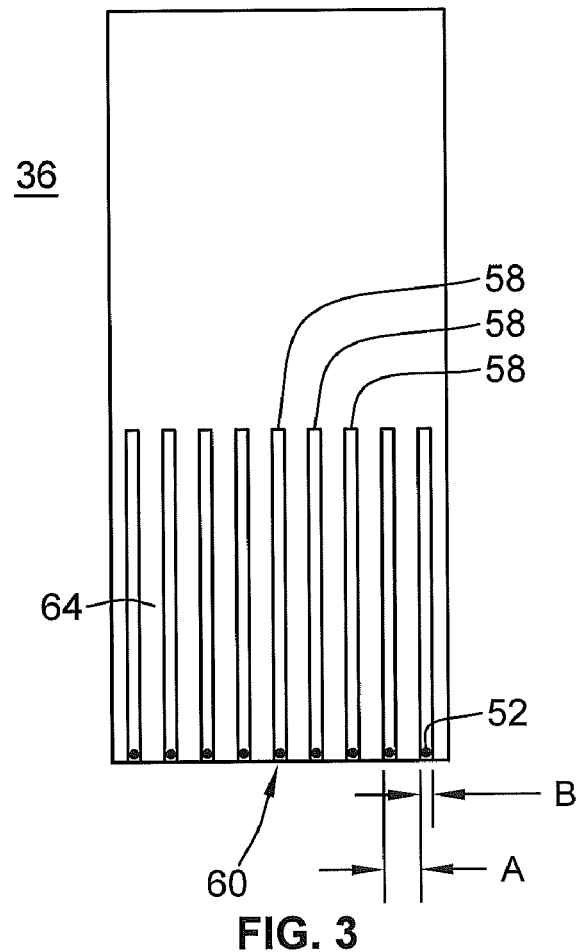
FIG. 3 is a top plan view of the mattress pad and sensors.
Figure 4:
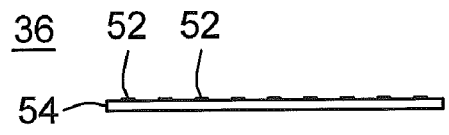
FIG. 4 is an elevation view of the mattress pad.

As can be seen in FIGS. 2, 3, and 7, a fastener 52 is pressed into each of the strips 58, providing an electrical connection therewith. Fastener 52 may be a male metallic snap fastener that functions as the connection point between the conductive fabric strips 58 and a connector harness 44.

The connector harness 44 links the array of strips 58 to either a wireless transmitter 40 or a standard, wired transmitter 46 (FIG. 1). As mentioned above, the transmitters 40, 46 function as a data collector and a transmitter of such data. In one embodiment, the harness 44 may include nine coaxial conductors approximately 30 inches in length. Each of the individual coaxial conductors is approximately ⅛ inch in diameter. At the end proximal to the mattress pad 54, each of the coaxial connectors is terminated by a ⅛ inch crimp-on ring terminal, which allows simple and secure attachment to the array of strips utilizing the female snap ring to capture the ring connector (not shown).

The end (not shown) of the harness 44 which attaches to the transmitter 40, 46 may include a D-Sub 15-pin male connector. Each of the nine coaxial center leads (not shown) may be individually crimped into a connector pin and inserted into locations within the connector back shell. Each of the nine outer shields from each coaxial conductor may be soldered with a "drain wire" or alternately, stripped and combined into a single termination which may be soldered together to ensure proper termination, and covered with a heat-shrink insulator. All nine drain wires may then be combined into a single conductor and crimped into the conductor as a tenth pin connector. Through the use of coaxial conductors, signal integrity to and from the array of strips 58 tend to be consistent and reliable during operation. The back shell (not shown) also permits the ability to monitor and verify whether the connector is securely attached to the transmitter 40, 46. A wire loop (not shown) can be configured to connect to two specific pins within the back shell. Alternately, a single wire may be used with the actual metallic back shell, used as the other conductor, and acting as a complete circuit when connected. When the wire completes the simple circuit within the transmitter 40, 46, the electronic circuitry will indicate that all systems are functional. Should the connector unfasten from the back of the transmitter 40, 46 the circuit will be broken, which will immediately flag the system 31, advising that the connection between the array of strips 58 and the transmitter 40 (or 46) has been broken.

The transmitters 40, 46 utilize electrical-field sensing technology combined with a programmable microcontroller that acts as the computing portion of system 31. The transmitter 40, 46 performs multiple functions by communicating with the array of sensors 36 and then transmitting this information to a remote database 39 (FIG. 1) for interpretation and review. The database 39 stores data for the facility, room groupings (wings, floor, building, etc.), rooms, and subjects 32. The database 39 also stores addressing and configuration information for the DCT units 40, 46. Finally, the database 39 also stores all of the logged information from the DCT units 40, 46.

The database 39 also stores other data related to the installation facility. This allows data to be correlated to the facility, facility zones, caregivers and subjects. The facility information is entered into the system 31 using a web browser. The interface is designed to allow very efficient data entry.

Each DCT 40, 46 generates a unique electrical-field to each of the nine strips 58 within the array of strips. As each of these strips 58 are energized with a very low electrical-field, within milliseconds, a unique signal is returned relative to the size and position of the subject 32 above the strip 58. In the present embodiment, this is performed continuously across all nine strips 58, taking full positional information twice every second. Any change in the position of the subject 32 generates a change in the electrical-field of the array of strips 58. Other schemes are also contemplated, such that sufficient information is collected to detect movement of the subject 32.

Once a transmitter 40, 46 has received the information from the array of strips 58, the information is converted into a digital code and sent via network to the central processor 38 (FIG. 1) for inclusion into a database 39 (FIG. 1) correlated to specific bed information, along with a time and date stamp. The transmitter 40, 46 is designed to be flexible in its data transmission mode and can be utilized in a hard wired or wireless network mode, as disclosed above.

Each transmitter 40, 46 can be powered by a 12-volt wall-mounted power supply capable of a maximum 500 milliamp current draw. Alternately, it is envisioned that an internal power source could be utilized in lieu of an external power source. Examples include lead acid, NiMH, and fuel cell type power sources. The transmitter 40, 46 also incorporates a solid state, resettable fuse insuring that the current will be cut off should there be any reason that current is drawn above the required power draw for the device. The housing for the transmitter may be formed by injection molding with ABS plastic having a flame retardant rating of UL94 V0.

Ethernet hub 50 can be a standard 10/100 hub that can be found at any computer or electronics store. Base station 42 can also be a standard wireless/hard-wired base station that can communicate, for example, over the 802.11 standard for wireless communications. It should be understood, however, that other configurations are within the scope of the invention, for example, base station 42 and Ethernet hub 50 could be combined into one device. System 31 can be configured to notify selected persons, i.e. nursing home or hospital management, via pagers 53, cell phones 51, e-mail 49, (see FIG. 1), fax, etc. through the Internet 47, wired or wireless or any suitable communication means or method.

System 31 can also be connected to the Internet 47 (FIG. 1) to permit remote access via either an in-house web page or a secure connection utilizing a standard web browser. The client interface may be entirely web browser based. The web pages may be served from a Windows Internet Information Server (IIS) using the PHP scripting language. The clients can see the data as pure standards based HTML without any special applications or plug-ins required. This allows any browser and operating system to access the system. Varying levels of access can be granted for access to the data stored by the system 31.

A software program manages the microcontroller, providing control of the electrical-field. It also routes the data out of the transmitter 40, 46 and into the network.

The central processor 38 functions in at least two capacities: data gathering into a database 39 (FIG. 1) stored in or in communication with central processor 38, and data interpretation and report generation. As mentioned above and discussed in further detail below, it is also contemplated that data interpretation and report generation may be performed by a web server.

The database 39 can track the data from each of the transmitters 40, 46 on a continuous basis. In the present embodiment, information from each strip 58 in the array of strips is stored and time stamped twice every second. The database 39 then stores the information and can group the information, for example, to track: (a) unique bed, floor/wing, and facility information relative to a caregiver's responsibility, (b) individual subject position data as a function of time, (c) transmitter information relating to IT addresses and other hardware characteristics, and (d) facility names and other identifiable characteristics.

The database 39 stores data from each transmitter 40, 46, which can be time-stamped for analysis and interpretation. Through the use of data analysis processes executed by software (detailed below) meaningful indicators can be established to confirm caregiver activity and the associated subject movement relative to specified medical orders. The output data may be selectable so as to provide a morning report giving a brief overview of caregiver performance on targeted subject rotations. Additionally, weekly and monthly performance reports may be created and can again be arranged by a particular caregiver.

In operation, the system 31 may be used as follows. A facility manager may review a status report displayed on or printed through central processor 38 upon his/her arrival at the beginning of the shift. Such a status report could show the performance of caregivers on the prior shift, as well as any movement of the subject 32. The report could correlate movement or caregiver-initiated movement with that ordered by a physician. Other reports may be executed that show movement over a longer period of time, or even that show performance of a particular caregiver over a period of time. Results could also be color coded, could be arranged by building wings or groups of rooms, or arranged in any other manner that is intuitive or preferred to the management. Information could be password protected in order to prevent the breach of security.

It is an advantage of the system 31 that no direct subject contact need occur and the system is nearly completely out of sight from the subject 32. In the event that the system 31 is disabled or switched off, no adverse side effects will occur since the system is not attached to the subject 32. Furthermore, the immediate health of the subject 32 is not dependent upon the operation of the system 31.

Figure 8:
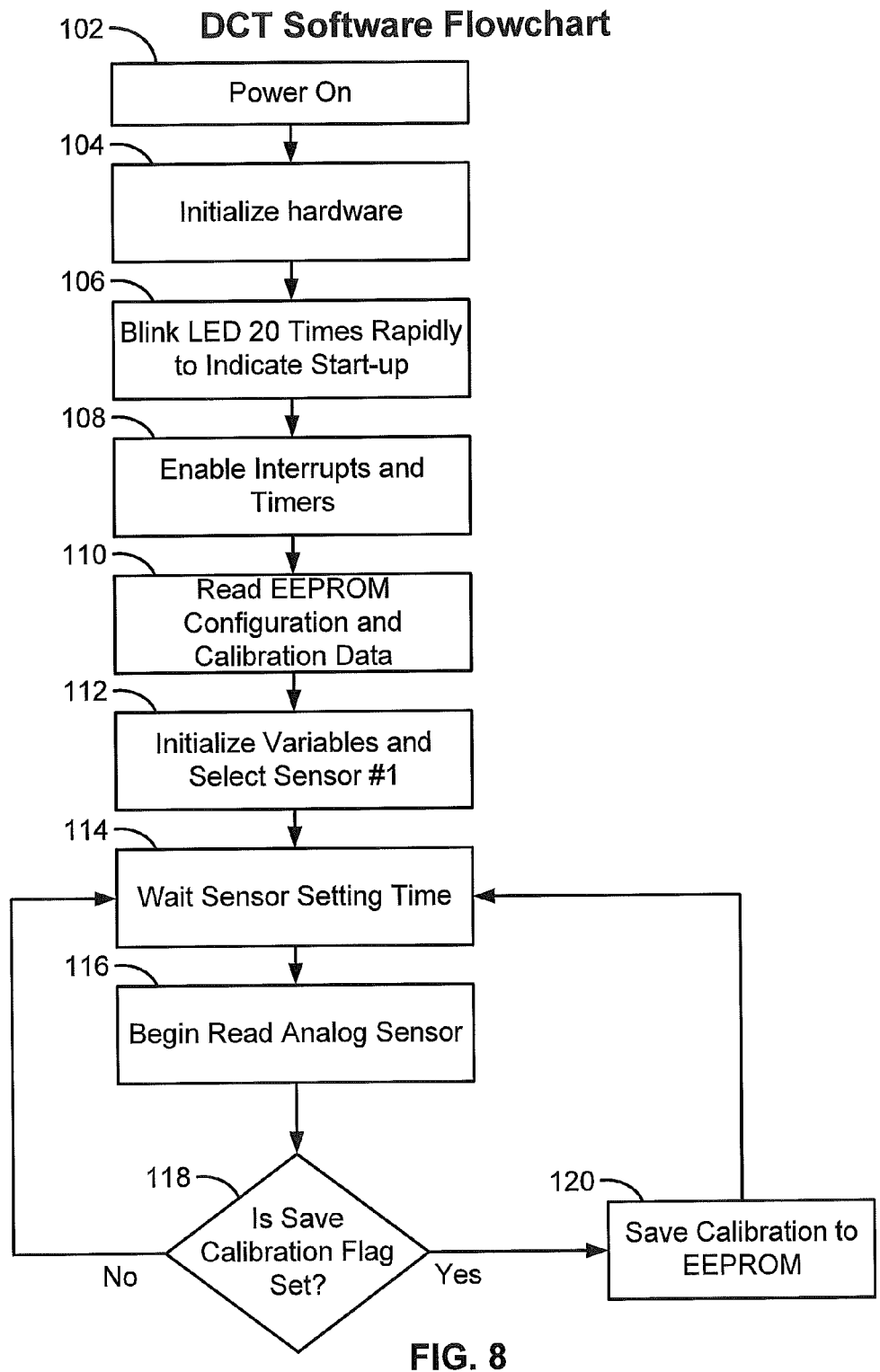
FIGS. 8-12 each show a subset of operational steps of a data collector transmitter and the software therefor according to a method of operation of the present invention.
Figure 12:
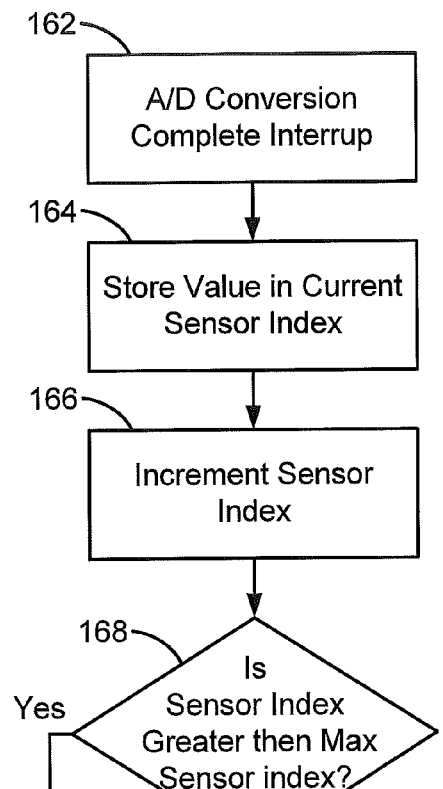

FIG. 8 shows the initialization sequence of the data collector transmitter (DCT). The DCT is powered on 102. The hardware portion of the DCT is initialized 104 and an indicator, such as an LED is used to indicate start-up, preferably by blinking on and off or by displaying a predetermined first color 106. Interrupts and timers are enabled 108. Configuration and calibration data is read 110, preferably off of a non-volatile device, such as non-volatile EEPROM. Variables are initialized and the first sensor is selected 112. The program then enters an infinite loop of reading the sensors in sequential order. The process waits a predetermined amount of time while the sensor settles 114. At step 116, the DCT begins to read the sensor. The microprocessor will generate an interrupt when the analog to digital conversion is complete. Before the process loops back to step 114, it checks to see if a completed calibration needs to be saved 118. If necessary, calibration is saved at step 120. When an analog to digital conversion completes, an interrupt occurs at step 162 (FIG. 12) and the value is saved to RAM 164. At this time, calibration calculation and/or digital filtering may occur, depending on the current mode of operation. The current sensor number is then indexed 166 to the next number. The sensor index is compared to the maximum sensor index 168. If the sensor index is greater than the maximum sensor index the sensor index is set to the sensor minimum 170. The interrupt exits at step 172.

Figure 9:
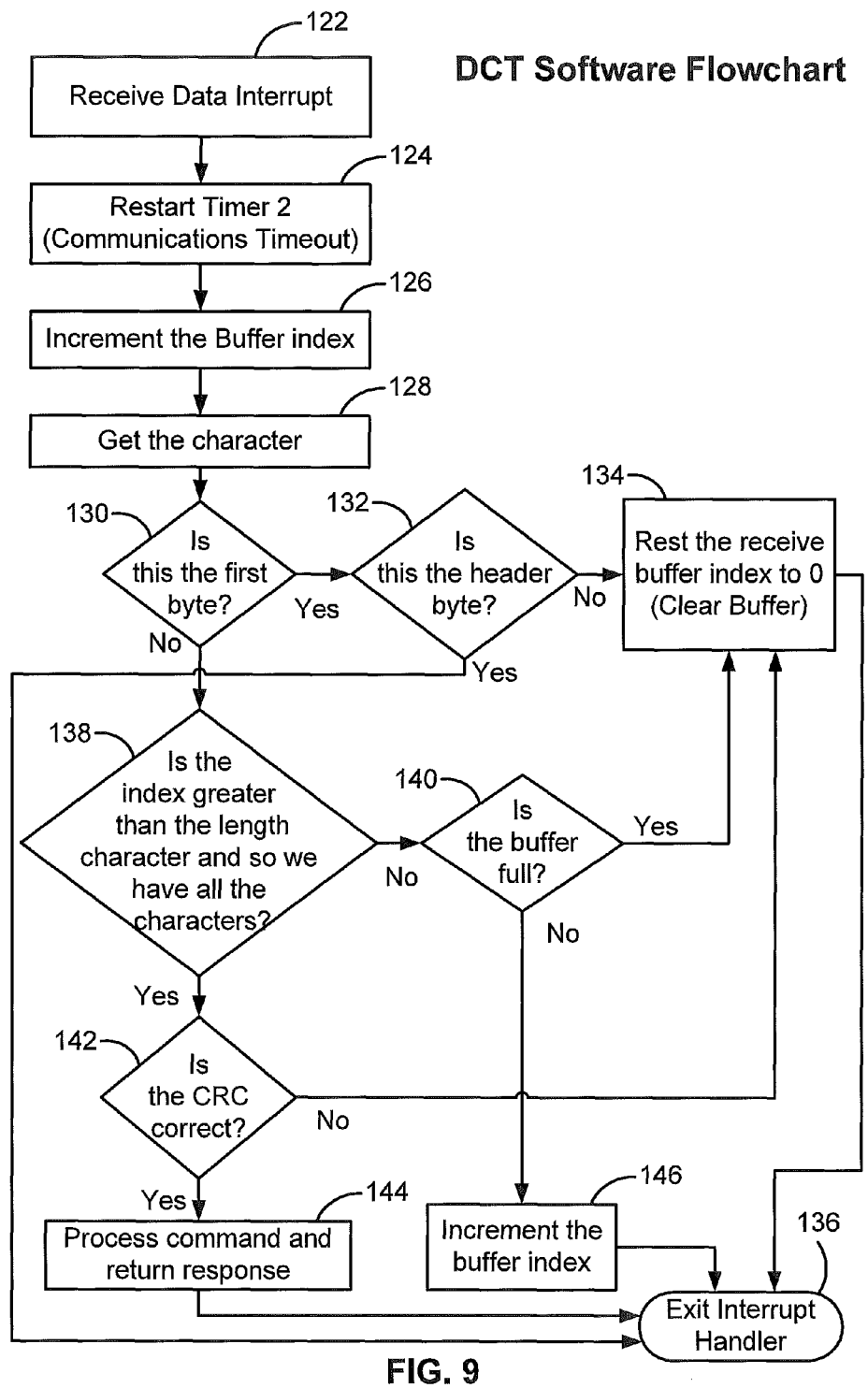
Figure 11:
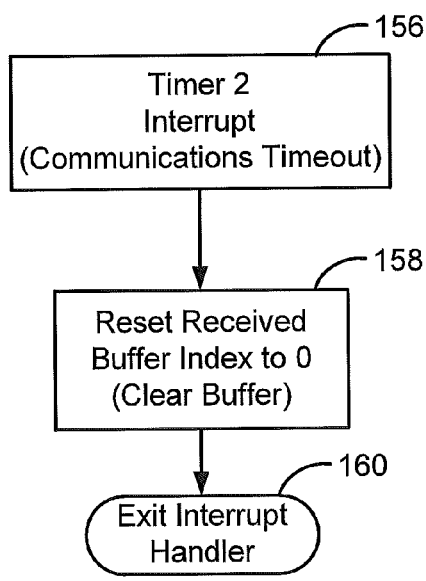

The serial data receive process is also interrupt based (FIG. 9). An interrupt is generated for each character received 122. A communication timer is restarted 124. The buffer index is incremented 126 and a character is gotten 128. The character is analyzed to determine if it is the first byte 130. If it is, the character is subsequently analyzed to determine if it is the header byte 132, if it is the header byte the interrupt exits 136. If at step 132 the character is determined not to be the header byte the buffer index is reset to zero 134 and the interrupt handler exits 136. More specifically, the timer interrupt occurs 156 after the receipt of each character to clear the buffer 158 if partial messages or erroneous data are received (FIG. 11). The interrupt exits at step 160.

Going back to step 130 if the character is determined not to be the first byte, a determination of whether the index is greater than the length character and whether all the characters are present is made 138. If the determination at step 130 is answered in the affirmative, the process proceeds to step 142 if not the process proceeds to step 140. At step 140 it is determined whether the buffer is full, if it is the buffer index is reset to zero 134 and the interrupt handler exits 136. If the buffer is not full the buffer index is incremented 146 and the interrupt handler exits 136. At step 142 it is determined whether the CRC (Cyclic Redundancy Check) is correct, if it is, the DCT processes the command and the response is returned 144 and the interrupt handler subsequently exits 136.

If at step 142 the CRC is found not to be correct, the buffer index is reset to zero 134 and the interrupt handler exits 136.

Figure 10:
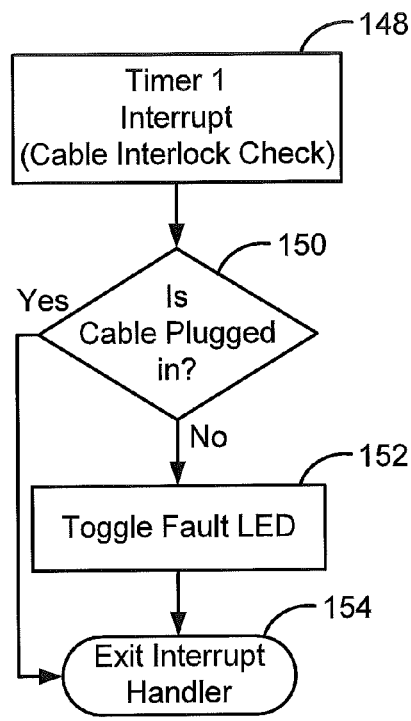

A general purpose timer (FIG. 10) also generates an interrupt on a periodic basis. On each of these interrupts 148, the DCT does a general status check to determine if any problems have occurred; such as sensor cable disconnection 150 or other communications errors. The fault LED will toggle state 152 at this time if a fault exists. If no problems have occurred the general purpose timer exits 154.

Figures 13, 14:
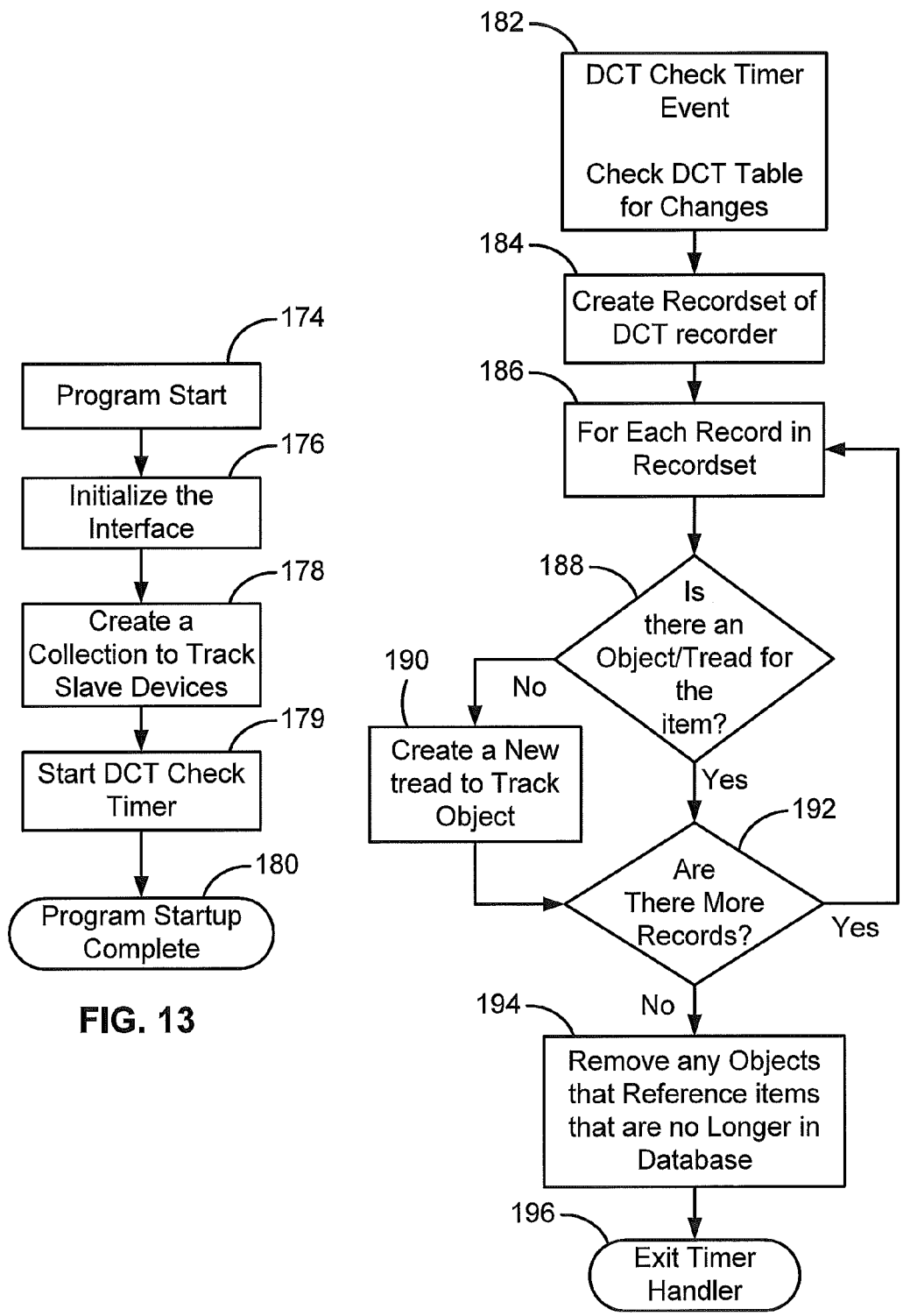

FIG. 13 shows the startup sequence of the data server. After startup 174, the graphical interface is initialized 176, and then a "collection" is created 178 to track the active slave devices (DCTs). A timer is started 179 that will periodically check the database to determine if new DCTs need to be added to the collection or if any need to be removed. The program startup is complete at step 180.

When the DCT check timer event occurs at step 182, (FIG. 14) the active DCT list is read from the database. Records of active DCTs are assembled into a recordset at step 184. The program iterates through the records at steps 186-192 to determine if any DCTs are new or need to be removed. More specifically, a record in the recordset is selected at step 186. At step 188, it is determined whether a corresponding object exists for the record. If no such object exists one is created at step 190. Once an object exists for the record, it is determined whether there are any additional records at step 192. If there is at least one such additional record, the program returns to step 186. If no such additional records exist at step 192, objects corresponding to non-active DCTs are removed at step 194. The timer hander exists at 196.

Each DCT is communicated with using its own program thread (FIG. 17). This prevents problems with other DCTs from affecting communication with other DCTs. At the creation of each thread 206, a log interval timer is set up 208. A network connection is then attempted to be established 210. This will loop forever until a connection is established 212 or the thread is terminated. The main server thread is informed of the current connection status of each thread 214, 216. If a connection is established, the log interval timer is then started 218 and the process exits 220.

Figure 15:
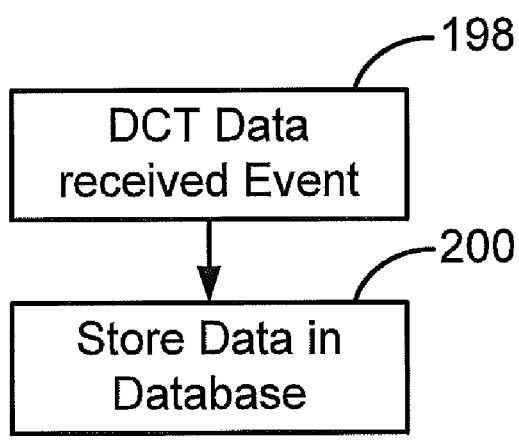
Figures 19, 20:
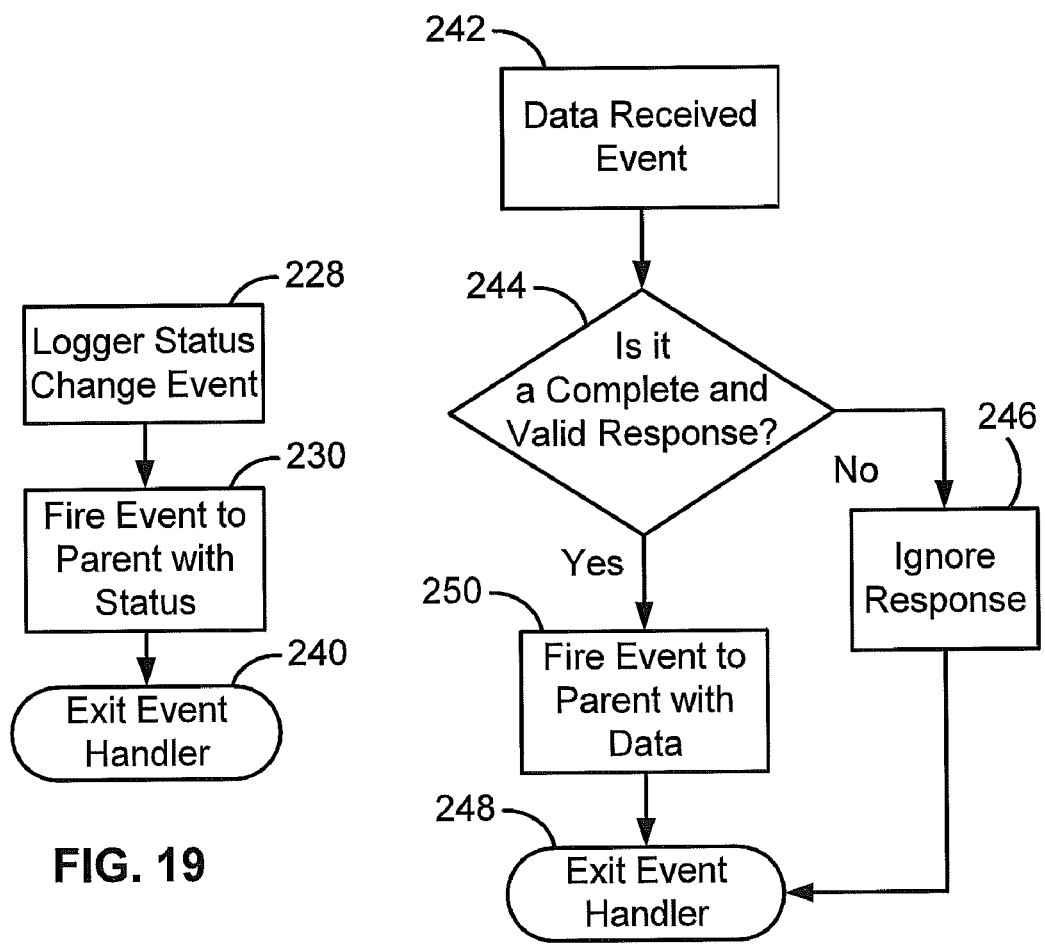

When a log timer event occurs 222, a message is sent 224 to the DCT requesting current sensor values as shown in FIG. 18. The thread will then wait until the data received event occurs at step 242 (FIG. 20). The message will be verified for integrity 244. If integrity is not present, the response is ignored 246. Valid data messages will generate an event 250 for the main server thread (FIG. 15).

Figure 16:
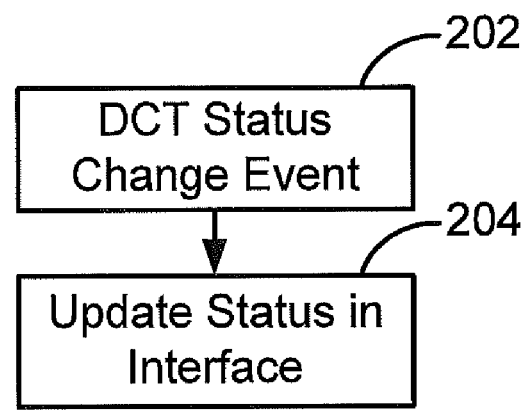

When DCT data received events occur at step 198, (FIG. 15) the server stores the data in the database, time stamped and tagged to the patient 200. When DCT threads detect a change in status of the DCT 202, it will generate a status change event 204 (FIG. 16). When these events occur, the main server thread updates the interface and writes to the database.

Shown in FIG. 19, when a status-change event occurs, the event handler starts at 228. Once started, the event handler sends the event and its status to the parent 230. The event handler then exits at 240.

Figure 21:
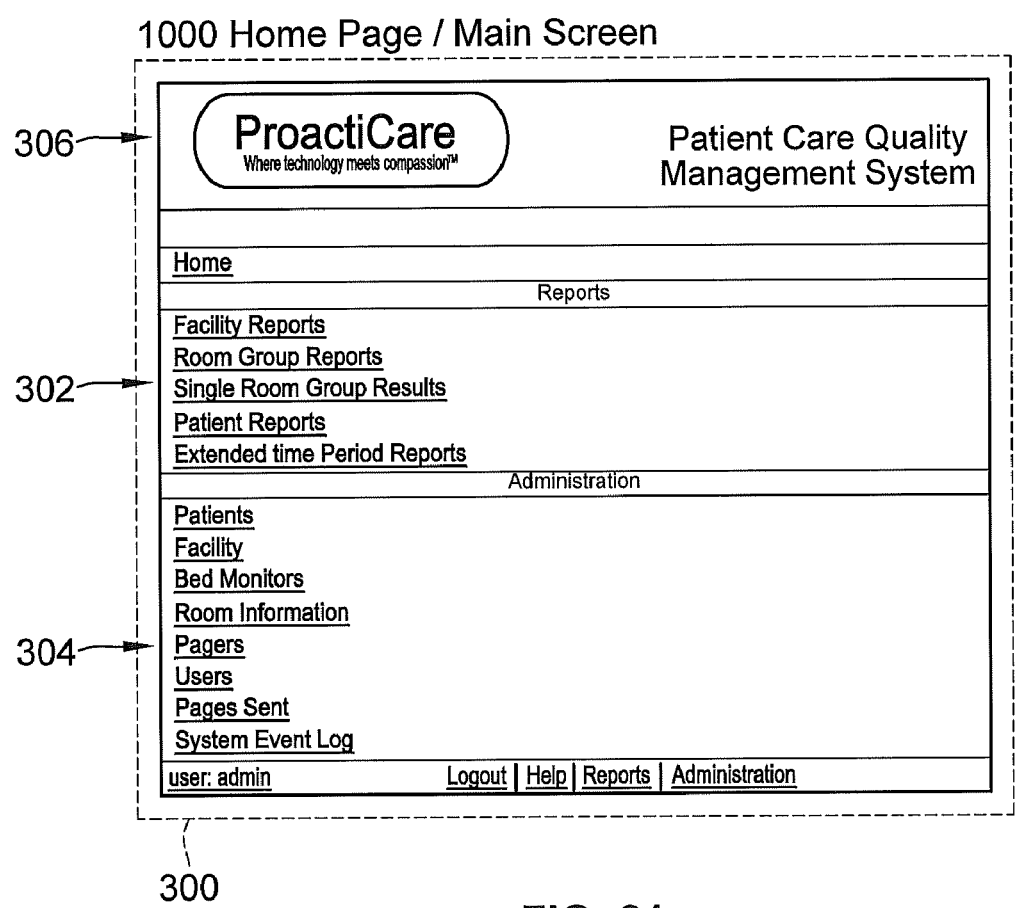
FIG. 21 shows a "Home Page" according to an embodiment of the present invention.

The system 31 user software is preferably designed to operate as a web based system with the functionality of being easily accessed on-site or from a remote location using a standard web browser, e.g., Microsoft Internet Explorer™ or an equivalent thereof. The browser enabled interface (see FIG. 21) is designed to operate independently from all other software elements within the system 31, including the "bed logs" database 39 and data collection from sensors 36, and DCTs 40, 46 portions of the overall system. The "Home Page" 300, shown in FIG. 21, is also the main screen which all users will first encounter when interfacing with the system 31.

The home page 300 is broken out into two main sections, a report generating portion 302 and administrative portion 304 including patient, monitor and room information. All of these individual sections may be password protected depending on the pre-determined authorization of the end-user. At any time within the various sub-menus, the logo 306 may be clicked which will take the user back to the home page 300.

An objective of the system 31 is to insure that while a patient is under the care of a healthcare professional; all rotations are performed at the specified intervals as dictated by medical orders. The system 31 will continuously provide critical caregiver performance data detailing the type of movement performed and most importantly time and date of these interactions insuring that a formal record of performance is established.

Figure 22:
FIG. 22 shows a "24 Hour Facility Activity Report Page" according to an embodiment of the present invention.

The "24 Hour Facility Activity Report," 310, FIG. 22, is intended to act as a quick facility scorecard, which will visually indicate overall performance of all assigned caregivers, relative to all rotations required throughout the entire facility duty shift. This record will be typically reviewed by a manager or supervisor at the end of a facility shift. Although the report described is based on a 24 hour duty cycle, additional reports will include other durations including real-time information, weekly or monthly performance indicators.

Three simple visual indicators 312 will show green, yellow or red, for example, describing level of performance within the facility. If the indicator is green, this may confirm that all rotations within the facility were performed according to specified medical orders. If the indicator is yellow, this may mean "caution" which points to the fact that specific patients may not have been rotated as required by medical orders and/or at the specified times. Additional investigation may be required to determine what had transpired during the interval under question. The red indicator may specify that there may have been significant portions of the patient rotation regimen not completed. Near the bottom of the page 314, the end user can click on the "View Room Groups" to drill down further into caregiver performance data relative to individual caregivers on specific floors or facility wings.

The View Room Groups screen 320 (FIG. 23) is designed to show room groupings within a facility, which are typically tied to a specific caregiver during their duty shift. This information will allow facility management to determine which specific rooms, beds and the specific patients that were not rotated during a set period of time.

Figure 26:
FIG. 26 shows a "Room Status Reports Page" according to an embodiment of the present invention.

The Patient, Monitor and Room Status Reports, 330, 340, and 350 (see FIGS. 24-26) are displays which provide the accurate and up to date information for the system 31. Patient Status Report 330 provides the location of the patient by both room and overall grouping. This insures that the information to be also tied back to the specific caregivers' responsible for these specific room groupings. The Monitor Status Report 340 advises which monitors are available for use within the facility and also which units are currently in service at the patient bedside. Additional information includes serial number, patient name that is tied to the DCT and IP address. Other information includes data collection intervals for each patient. The Room Status Report 350 details patient name, Data Collector Transmitter (DCT) serial number, room number and overall room grouping.

The Patient Administration Entry Form 360 (see FIG. 27) provides a simple and effective method to enter patient data into the system records of the database 39. Additional information required includes Room Group, Room Number, turn frequency (default 120 minutes) and allowable turn window (e.g., 15 minutes). Ideally a patient should be rotated precisely at the prescribed turn frequency, for example every two hours, however, due to actual workload and other demands on caregiver time; they may not be able to rotate a patient at an exact time interval. The allowable turn window will provide an additional time range which allows the caregiver to perform a specified or required rotation within a pre-set time interval, for example 15 minutes beyond the two hour turn frequency. Should a patient remain unturned beyond the established turn window interval, the system will "flag" this record providing the manager with an indicator that the caregiver has missed a turn. The entry form also allows editing of the patient information in the event the patient changes rooms or leaves the facility.

The New Bed Monitor Entry Form 370 (see FIG. 28) is intended to allow facility managers to add new monitor devices to the facility. It also allows several selectable functions regarding data transmission via either hardwired or wireless link. Other features include assignable query rate, maximum log intervals, patient info and activation check box (turn on or turn off communication with DCT). This entry form also allows editing of existing monitor information.

The Edit Room Groups Form 380 (see FIG. 29) allows easy addition, modification or deletion of specific room groupings. Typically these room groups will be tied directly to specific caregiver room assignments within a facility, thus tying the assigned caregiver to their grouping of rooms. Once the room groups are set, only patient rooms falling within these groups will be in the dropdown menu. For example if there is a "South Room Group" only specific rooms that are pre-assigned during setup will be within the dropdown menu. Other rooms within the facility will be tied to their proper, pre-determined room group. In addition, a full report may be viewed detailing all room groups within a facility.

Figure 30:
FIG. 30 shows an "Edit Room Administration Page" according to an embodiment of the present invention.

The Edit Room Administration Form 390 (see FIG. 30) will allow a facility manager to add, modify or delete rooms within a specific room group. There is also a feature to view the specific rooms and how they relate to specific room groups.

Other features such as data export, import, analysis and graphic visualizations may be considered important in the expansion and enhancement of the system 31.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

There is a plurality of advantages of the present invention arising from the various features of the subject monitoring system and associated method described herein. It will be noted that alternative embodiments of the subject monitoring system and associated method of the present invention may not include all of the features described yet still benefit from at least some of the advantages of such features. Those of ordinary skill in the art may readily devise their own implementations of a subject monitoring system and associated method that incorporate one or more of the features of the present invention and fall within the spirit and scope of the present invention as defined by the appended claims.

What is claimed is:

1. A system for monitoring a subject, the system comprising:
- a plurality of beds, each bed of said plurality of beds including a data collector transmitter and a sensor array wherein said sensor array includes a plurality of sensor units;
- each sensor unit of said plurality of sensor units provides data to said data collector transmitter wherein the data is transmitted by said data collector transmitter to a central processor at wide intervals when no movement by the subject is sensed and the data is transmitted to said central processor at rapid intervals when movement by the subject is sensed, wherein said central processor connects each bed of said plurality of beds in a network;
- a database of said central processor stores the data from each bed of said plurality of beds received from said data collector transmitter, wherein the data includes date data, time data, and position data of the subject within each bed of said plurality of beds;
- said central processor interprets the data to detect a change in position of the subject within each bed of said plurality of beds and generates a report providing caregiver performance data of at least one caregiver, wherein the caregiver performance data includes caregiver-initiated movement of the subject within each bed of said plurality of beds in the network.

2. The system for monitoring a subject of claim 1, wherein the database further stores a unique address of said data collector transmitter and a communication rate of said data collector transmitter.

3. The system for monitoring a subject of claim 1, wherein the data further includes at least one selected from the group of facility, wing, floor, building, and room related to each bed of said plurality of beds.

4. The system for monitoring a subject of claim 1, wherein the position data of the subject is determined by a change in an electrical field of said sensor array.

5. The system for monitoring a subject of claim 1, wherein said data collector transmitter is wireless.

6. The system for monitoring a subject of claim 1, wherein the caregiver performance data further includes a correlation of the caregiver-initiated movement of a subject relative to that ordered by a physician.

7. The system for monitoring a subject of claim 1, wherein the report further includes a scorecard, and uses a web-based interface with visual indicators of overall performance of at least one caregiver.

8. The system for monitoring a subject of claim 1, wherein the data collector transmitter transmits the data of said sensor array to said central processor using at least one protocol selected from the group comprising LAN-based data transmission, wireless data transmission, infrared transmission, ZigBee mesh network, Bluetooth™ transmission, and radio frequency transmission.

9. The system for monitoring a subject of claim 1 further comprising a web browser enabled user interface, wherein said web browser enabled user interface permits remote access to the report.

10. The system for monitoring a subject of claim 1 further comprising a notification of caregiver-initiated movement of a subject, wherein said notification is communicated through at least one selected from the group of a pager, a cell phone, an electronic-mail, or a facsimile.

11. The system for monitoring a subject of claim 1, wherein said sensor array is configured to be between said bed and said subject when said subject is on said bed.

12. The system for monitoring a subject of claim 1, wherein said sensor array comprises soft conductive material.

13. The system for monitoring a subject of claim 1, wherein said sensor array is positioned on a mattress pad.

* * * * *